(12) United States Patent
Feinberg et al.

(10) Patent No.: US 10,653,517 B2
(45) Date of Patent: May 19, 2020

(54) ADJUSTABLE IMPLANT

(71) Applicant: Ethicon, Inc., Somerville, NJ (US)

(72) Inventors: Marc Feinberg, Ringoes, NJ (US);
James Fleming, Bethlehem, PA (US)

(73) Assignee: MENTOR WORLDWIDE LLC, Irvine, CA (US)

(*) Notice: Subject to any disclaimer, the term of this patent is extended or adjusted under 35 U.S.C. 154(b) by 30 days.

(21) Appl. No.: 15/807,017

(22) Filed: Nov. 8, 2017

(65) Prior Publication Data

US 2019/0133751 A1 May 9, 2019

(51) Int. Cl.
*A61F 2/12* (2006.01)

(52) U.S. Cl.
CPC ........ *A61F 2/12* (2013.01); *A61F 2250/0003* (2013.01); *A61F 2250/0004* (2013.01)

(58) Field of Classification Search
CPC ....................................................... A61F 2/12
USPC ....................................................... 623/7–8
See application file for complete search history.

(56) References Cited

U.S. PATENT DOCUMENTS

| | | |
|---|---|---|
| 1,146,805 A | 1/1874 | Cox |
| 1,091,063 A | 3/1914 | Hutchinson |
| 1,263,798 A | 4/1918 | Otto |
| 3,852,833 A | 12/1974 | Köneke et al. |
| 3,919,724 A | 11/1975 | Sanders et al. |
| 3,934,274 A | 1/1976 | Hartley, Jr. |

(Continued)

FOREIGN PATENT DOCUMENTS

| | | |
|---|---|---|
| DE | 19923183 A1 | 11/2000 |
| EP | 1 547 549 A2 | 6/2005 |

(Continued)

OTHER PUBLICATIONS

Becker Expander/Mammary Prostheses (Reconstruction Adjunct Study) Mentor, 2002 <http://www.mentorwwllc.com/Documents/Becker.pdf>.

(Continued)

*Primary Examiner* — Suzette J Gherbi
(74) *Attorney, Agent, or Firm* — Etan S. Chatlynne; Roberts Calderon Safran & Cole P.C.

(57) ABSTRACT

Various embodiments of an adjustable implant are disclosed herein. The adjustable implant comprises a hydraulic mechanism disposed within the shell, which includes a first component and a second component that is moveable with respect to the first component, and a band with a first and second end disposed within the shell in a round (e.g., elliptical) configuration having a second diameter in the plane that is less than the first diameter. In some embodiments, the first end of the band may be connected to the first component and the second end of the band may be connected to the second component. In some embodiments, the mechanism may include a fluid and a pump that has a first actuator comprising a first chamber and a second actuator comprising a second chamber. Depressing the first actuator causes the first component to move in a first direction, which reduces the diameter of the band and increases the height of the implant. Depressing the second actuator causes the first component to move in a direction opposite the first direction, which increases the diameter of the band and decreases the height of the implant.

16 Claims, 6 Drawing Sheets

(56) References Cited

U.S. PATENT DOCUMENTS

| | | |
|---|---|---|
| 4,433,440 A | 2/1984 | Cohen |
| 4,615,704 A | 10/1986 | Frisch |
| 4,624,671 A | 11/1986 | Kress |
| 4,643,733 A | 2/1987 | Becker |
| 4,773,908 A | 9/1988 | Becker |
| 4,775,379 A | 10/1988 | Fogarty et al. |
| 4,790,309 A | 12/1988 | Becker |
| 4,944,749 A | 7/1990 | Becker |
| 4,969,892 A | 11/1990 | Burton et al. |
| 4,969,898 A | 11/1990 | Calogero |
| 4,969,899 A | 11/1990 | Cox, Jr. |
| 5,019,101 A | 5/1991 | Purkait et al. |
| 5,181,907 A | 1/1993 | Becker |
| 5,219,360 A | 6/1993 | Georgiade |
| 5,507,808 A | 4/1996 | Becker |
| 5,549,672 A | 8/1996 | Maddock et al. |
| 5,630,843 A | 5/1997 | Rosenberg |
| 5,723,006 A | 3/1998 | Ledergerber |
| 5,776,159 A | 7/1998 | Young |
| 6,113,569 A | 9/2000 | Becker |
| 6,183,514 B1 | 2/2001 | Becker |
| 6,540,702 B1 | 4/2003 | Sarango |
| 6,755,861 B2 | 6/2004 | Nakao |
| 7,081,136 B1 | 7/2006 | Becker |
| 7,615,074 B2 | 11/2009 | Carvalio |
| 7,762,982 B1 | 7/2010 | Shah |
| 8,080,057 B2 | 12/2011 | Kronowitz |
| 8,197,542 B2 | 6/2012 | Becker |
| 8,202,317 B2 | 6/2012 | Becker |
| 8,308,630 B2 | 11/2012 | Birk et al. |
| 8,394,118 B2 | 3/2013 | Jones et al. |
| 8,398,710 B2 | 3/2013 | Forsell |
| 9,265,921 B2 | 2/2016 | Korman |
| 2002/0011497 A1 | 1/2002 | Farris |
| 2005/0284215 A1 | 12/2005 | Falsetti |
| 2006/0100578 A1 | 5/2006 | Lieberman |
| 2006/0161196 A1 | 7/2006 | Widgerow |
| 2007/0050026 A1 | 3/2007 | Carvalio |
| 2008/0275569 A1 | 11/2008 | Lesh |
| 2009/0210056 A1 | 8/2009 | Forsell |
| 2010/0010531 A1 | 1/2010 | Shalon et al. |
| 2010/0010871 A1 | 1/2010 | Mengerink |
| 2010/0087843 A1 | 4/2010 | Bertolote et al. |
| 2010/0108717 A1 | 5/2010 | Szymanski |
| 2010/0204792 A1 | 8/2010 | Greco |
| 2010/0228347 A1 | 9/2010 | Schuessler |
| 2010/0324688 A1* | 12/2010 | Doty .................... A61F 2/4425 623/17.16 |
| 2011/0106249 A1 | 5/2011 | Becker |
| 2011/0153017 A1 | 6/2011 | McClellan |
| 2011/0160854 A1 | 6/2011 | Berg et al. |
| 2011/0160859 A1* | 6/2011 | Doty .................... A61F 2/4425 623/17.13 |
| 2011/0230845 A1* | 9/2011 | Pascal ................ A61M 39/045 604/249 |
| 2011/0264213 A1 | 10/2011 | DeMiranda |
| 2012/0116509 A1* | 5/2012 | Forsell .................... A61F 2/12 623/8 |
| 2013/0007980 A1 | 1/2013 | Worker et al. |
| 2013/0013063 A1 | 1/2013 | Del Vecchio |
| 2013/0013084 A1 | 1/2013 | Birk |
| 2013/0079807 A1 | 3/2013 | Korman |
| 2013/0237915 A1 | 9/2013 | Barrelli |
| 2013/0245758 A1 | 9/2013 | Chitre et al. |
| 2013/0341353 A1 | 12/2013 | Harris |
| 2014/0031619 A1 | 1/2014 | Moon |
| 2014/0100656 A1 | 4/2014 | Namnoum et al. |
| 2014/0156001 A1 | 6/2014 | Davodian |
| 2014/0200396 A1* | 7/2014 | Lashinski .......... A61B 17/0401 600/37 |
| 2014/0236210 A1* | 8/2014 | Payne .................... A61B 90/02 606/192 |
| 2015/0038976 A1 | 2/2015 | Roschak et al. |
| 2016/0228603 A1 | 8/2016 | Nguyen et al. |
| 2016/0250017 A1 | 9/2016 | McClellan |
| 2016/0310711 A1 | 10/2016 | Luxon et al. |
| 2017/0079737 A1 | 3/2017 | Jones et al. |
| 2017/0127929 A1 | 5/2017 | Schutt et al. |
| 2017/0165025 A1* | 6/2017 | Payne .................... A61B 90/02 |
| 2017/0333179 A1* | 11/2017 | Forsell .................... A61F 2/12 |
| 2018/0153684 A1* | 6/2018 | Van Heugten ........ A61F 2/1624 |
| 2018/0200714 A1 | 7/2018 | Viovy et al. |
| 2018/0279889 A1 | 10/2018 | Lee |
| 2019/0091001 A1* | 3/2019 | Forsell ................ A61B 90/361 |
| 2019/0111206 A1* | 4/2019 | Forsell ................ A61M 1/127 |
| 2019/0223971 A1 | 7/2019 | Payne et al. |

FOREIGN PATENT DOCUMENTS

| | | |
|---|---|---|
| EP | 2453839 B1 | 3/2014 |
| WO | 95/04561 A1 | 2/1995 |
| WO | 2016003718 A1 | 1/2016 |

OTHER PUBLICATIONS

Extended European Search Report for European Application No. 17158382.6-1664, dated Jul. 27, 2017, 8 pages.

International Search Report and Written Opinion for International Application No. PCT/IB2018/056354, dated Nov. 16, 2018, 12 pages.

* cited by examiner

ADJUSTABLE IMPLANT

CROSS-REFERENCE TO CO-PENDING APPLICATION

This application is a counterpart of U.S. patent application Ser. No. 15/693,965, filed Sep. 1, 2017, which is incorporated by reference herein in it entirety.

FIELD

The subject matter disclosed herein relates to breast implants for use in a subject.

BACKGROUND

Tissue expanders are used to assist in stretching skin of a subject to provide a tissue pocket or capsule having an appropriate size to accommodate a permanent implant, such as a breast implant. In typical usage, the tissue expander is implanted into a subject to help prepare the subject to receive a permanent breast implant. The tissue expander may be expanded by introducing additional material therein, e.g., saline, until the desired size of the pocket or capsule is achieved, at which point the tissue expander may be removed. A permanent breast implant may then be implanted into the subject.

Certain tissue expanders may be used as an adjustable breast implant, such as the Becker Expander/Mammary Prostheses manufactured by Medtronic of Irvine, Tex. This adjustable implant utilizes a fill tube through which saline may be introduced or removed from the implant to change the implant's size. Thus, the adjustable implant may be used to change the size of the capsule. Once the desired size of the capsule is achieved, the fill tube may be removed from the implant, thereby rendering the implant non-adjustable. The implant may remain in the capsule.

SUMMARY

Various embodiments of an adjustable implant are disclosed herein. In some embodiments, the adjustable implant comprises: a shell that has a first membrane and a base that includes a first diameter in a plane parallel to the base, a hydraulic mechanism disposed within the shell, which includes a first component and a second component that is moveable with respect to the first component, and a band with a first and second end disposed within the shell in a round (e.g., elliptical) configuration having a second diameter in the plane that is less than the first diameter. In some embodiments, the first end of the band may be connected to the first component and the second end of the band may be connected to the second component. In some embodiments, the mechanism may include a fluid and a pump that has a first actuator comprising a first chamber and a second actuator comprising a second chamber.

In certain embodiments, the first component may be a barrel and the second component may be a piston disposed at least partially within the barrel. The piston may include or be connected to a plunger rod and a plunger cap, and the barrel may include or be connected to a barrel cap, a first port, and a second port. The mechanism may also include a first tube connected between the first chamber and the first port and a second tube connected between the second port and the second chamber. The mechanism may also include a biasing member in the barrel between the piston and the barrel cap. The mechanism may also include a barrel connecting the first chamber to the second chamber. The second actuator of the mechanism may include or be connected to a finger for opening a valve disposed in the second tube.

In various embodiments, the adjustable implant may also comprise a loop through which the band is disposed. The loop may be attached to the first membrane. In some embodiments, the shell may also include a second membrane surrounding the first membrane.

In other embodiments, an adjustable implant may comprise a shell including a first membrane filled with an elastomer. A hydraulic mechanism, which includes a pump, piston, and barrel, may be disposed within the shell. An adjustable band with a first end and a second end may be disposed therein in a round configuration with the first end connected to the barrel and a second end connected to the piston. The band may be disposed through a loop. The loop may be attached to the first membrane. A second membrane may surround the first membrane.

Also disclosed herein are exemplary methods of using an adjustable implant. In these methods, the adjustable implant is provided. The adjustable implant may have a height and it may include therein an adjustable band having a round configuration, a diameter, a first end, and a second end. The implant may also include a hydraulic mechanism that comprises a fluid, a pump that has a first actuator including a first chamber and a second actuator including a second chamber, a barrel that has a barrel cap, a first port, a second port, and, piston, which has a plunger rod and plunger cap, that is at least partially disposed within the barrel. The first end of the band may be connected to the barrel cap and the second end of the band may be connected to the plunger cap. The implant may also include a shell that has a base and a first membrane, and may also include a first diameter in a plane parallel to the base.

The diameter of the band may be decreased in order to increase the height of the implant. The diameter of the band may be increased in order to decrease the height of the implant. The diameter of the band may be decreased by depressing the first actuator. The diameter of the band may be decreased by depressing the first actuator, which advances fluid into the barrel and causes the piston, plunger cap, and the second end of the band to move in a first direction. The diameter of the band may be increased by depressing the second actuator. The diameter of the band may be increased by depressing the second actuator, which causes the piston, plunger cap, and the second end of the band to move in a direction opposite the first direction.

BRIEF DESCRIPTION OF THE DRAWINGS

While the specification concludes with claims which particularly point out and distinctly claim the subject matter described herein, it is believed the subject matter will be better understood from the following description of certain examples taken in conjunction with the accompanying drawings, in which like reference numerals identify the same elements and in which:

DETAILED DESCRIPTION

The following description sets forth certain illustrative examples of the claimed subject matter. Other examples, features, aspects, embodiments, and advantages of the technology should become apparent to those skilled in the art from the following description. Accordingly, the drawings and descriptions should be regarded as illustrative in nature.

Figure 1:
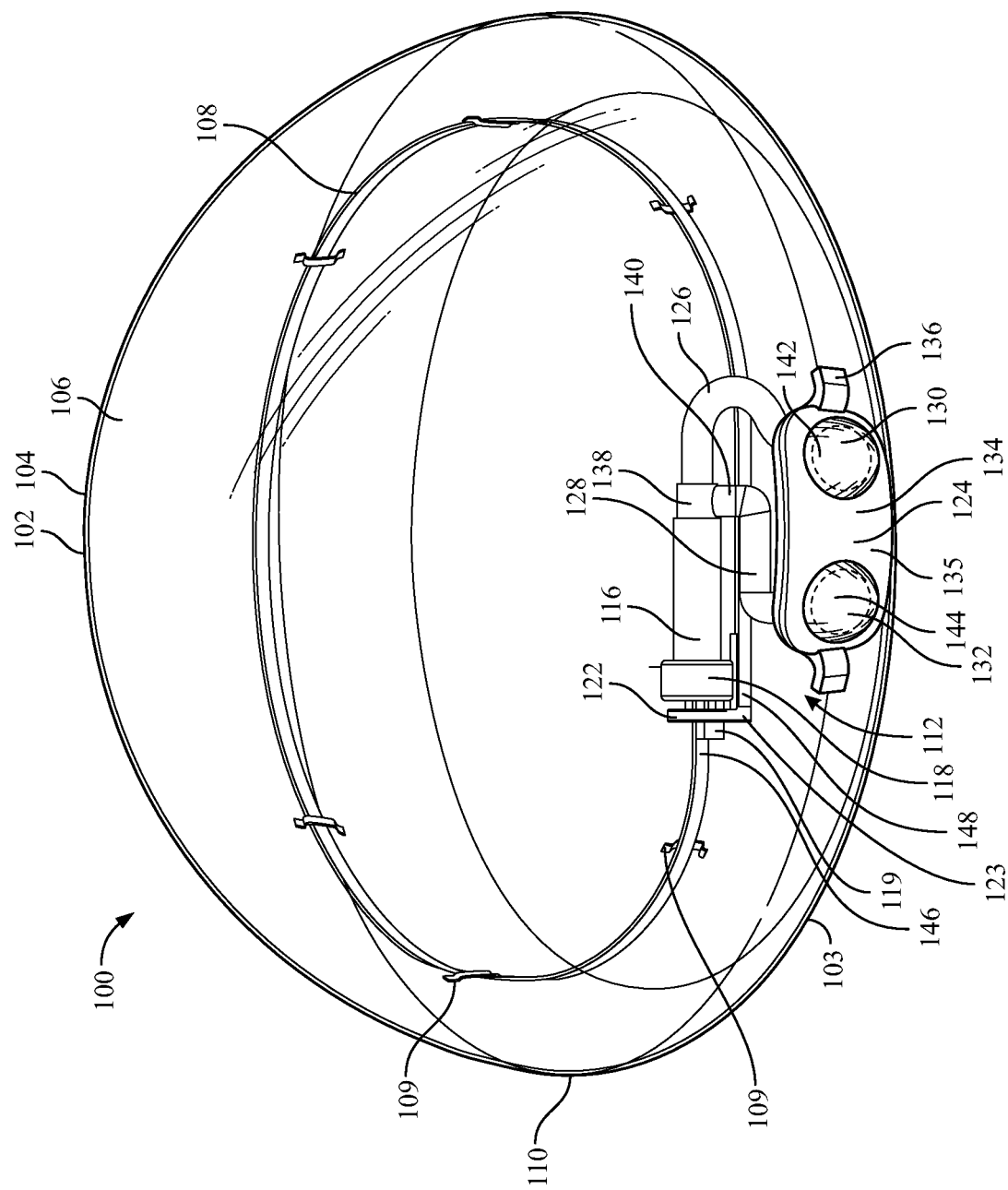
FIG. 1 depicts a perspective view of an adjustable implant having an original profile.

FIG. 1 is a representation of an exemplary embodiment of the present subject matter, i.e., adjustable implant 100. Adjustable implant 100 includes a shell 102, which includes a base 103. Shell 102 includes a shell membrane 104 that may be fabricated from any resilient and/or stretchable material used to fabricate conventional implants, particularly breast implants. For example, elastomeric silicones, such as silicone rubber, may be used to fabricate shell membrane 104. Shell 102 may be filled with a material 106 to maintain a desired form and prevent shell membrane 104 from collapsing and deforming under its own weight. In some embodiments, shell 102 has the form of a conventional breast implant, which is the form of shell 102 reflected in the figures. Further, material 106 may provide compliance and/or resiliency when shell membrane is subject to external forces generated by, e.g., foreign objects or a subject's anatomy. The material 106 may be, e.g., an elastomer, such as silicone rubber, a silicone gel, or a liquid, such as saline.

Adjustable implant 100 additionally includes a flexible band 108 made of e.g., elastic, rubber, or plastic. Alternatively, it may be a fluoropolymer, such as Teflon, which may provide certain advantages over other alternatives including low friction and bacterial resistance. Band 108 may have a round configuration, including, but not limited to an elliptical (including circular) configuration, ovular configuration, annular configuration, disk configuration or spherical configuration. Further, it may be oriented such that it may be parallel or nearly parallel to base 103 of implant 100. The configuration of band 108 includes a diameter θ that is less than the diameter of a circumferential portion 110 of shell 102 that is coplanar with band 108. In certain embodiments, the plane including circumferential portion 110 and band 108 also includes the maximum diameter of implant 100. That is, band 108 is disposed in a plane where implant 100 is widest. Loops 109 may be provided within material 106 in a round or elliptical configuration. Loops 109 may additionally be attached to an inner surface of shell membrane 104. Band 108 may be disposed within loops 109 in a manner similar to a belt in belt loops on a pair of pants. In some embodiments, a sheath (not shown) for band 108 may be provided. In these embodiments, band 108 may be disposed within the sheath and the sheath may be disposed through loops 109. The sheath may be fabricated from any material that is also suitable for fabricating band 108, such as Teflon.

Implant 100 may have a maximum diameter ranging between approximately three inches and seven inches. In some embodiments, the maximum diameter θ of band 108 is approximately 0.2 inches to 1 inch less than the maximum diameter of implant 100. Band 108 may be a thin strip having a thickness of between approximately 0.03 inches and 0.15 inches. Band 108 may have a height of between approximately 0.25 inches and 1 inch.

Diameter θ of band 108 may be decreased or increased. When θ is decreased, band 108 squeezes material 106, which causes a corresponding increase in height of shell 102. Further, in those embodiments including loops 109, band 108 displaces loops 109, which may further facilitate squeezing material 106 by evenly distributing the constrictive forces upon material 106 caused by reducing diameter θ. Further, in those embodiments where loops 109 are attached or bonded to the inner surface of shell membrane 104, shell membrane 104 may further distribute the constrictive forces. When θ is increased, band 108 releases the portion of material 106 that was being squeezed, which causes a corresponding decrease in the height of shell 102. In some embodiments, the height of shell 102 may be increased by between approximately 0.2 inches and 2 inches. In certain embodiments, the height of shell 102 may be increased by approximately 0.5 inches.

A hydraulic mechanism 112 may be embedded within material 106 of implant 100 and coupled to band 108 for changing the diameter θ of band 108. Mechanism 112 may be controlled by a subject in which implant 100 is implanted (as opposed to requiring manipulation by a health care professional). Although the discussion herein is limited to hydraulic embodiments, pneumatic embodiments may also be suitable.

Figure 2:
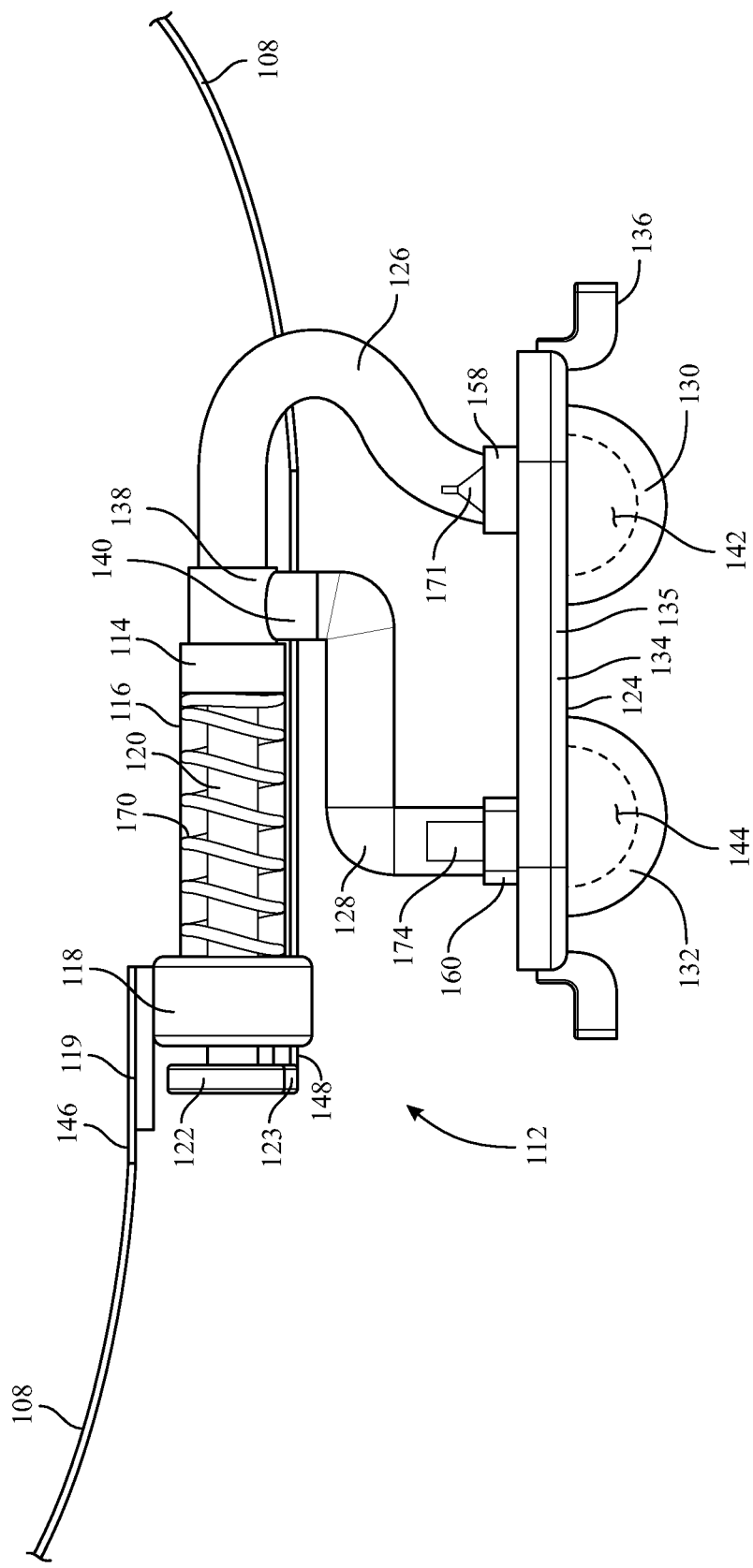
FIG. 2 depicts a magnified top view of a hydraulic mechanism within the adjustable implant of FIG. 1.

Mechanism 112 is detailed in FIG. 2, which shows certain components as transparent, enabling view of other components and features therein. Mechanism 112 includes various components and features that may be moved or manipulated relative to other components and features of mechanism 112 and implant 100. Stationary components and features include, among others, a piston cylinder or barrel 116, and barrel cap 118. Barrel 116 may have an internal volume of between approximately 1 milliliter and 30 milliliters. In certain embodiments, barrel 116 has a volume of approximately 10 milliliters. Moveable components and features may include, among others, a piston 114, a plunger rod 120 connected to piston 114, and a plunger cap 122. Mechanism 112 also includes a pump 124, a first tube 126, and a second tube 128. Pump 124 may further include a first or filling actuator 130, a second or emptying actuator 132 and a pump body 134. In some embodiments, pump body 134 may include a face plate 135 and tabs 136. In some embodiments, face plate 135 may include filling actuator 130 and emptying actuator 132. Further, barrel 118 may include a tip or first port 138 and a second port 140, which in some embodiments may be disposed through barrel 116, proximate tip or first port 138. Further, a biasing mechanism (e.g., spring) 170, may be disposed about plunger rod 120 between piston 114 and barrel cap 118. In some embodiments, biasing member 170 may apply a spring force to piston 114 in the direction of tip 138.

Tabs 136 assist in maintaining the position of pump 108 relative to other components of implant 100 by resisting forces applied to pump 124, particularly forces applied to filling actuator 130 and emptying actuator 132. In some embodiments not shown, pump 124 may be positioned near to the bottom of shell 102, i.e., proximate base 103. As shown in the figures, face plate 135 is substantially parallel to the portion of shell membrane 104 closest thereto. In some embodiments, not shown, face plate 135 may be angled away from the bottom of the shell relative to the position shown in the figures. This angle may be between approximately 10 degrees and 80 degrees, it may be between approximately 30 degrees and approximately 60 degrees, it may be approximately 45 degrees, or it may be some other range of angles between 10 degrees and 80 degrees. So positioned and oriented, anatomy of a subject may provide further resistance to forces applied to pump 124. For example, where implant 100 is a breast implant, bones in the chest may resist displacement of pump 124, thereby facilitating a subject's ability to manipulate filling actuator 130 and emptying actuator 132.

Filling actuator 130 may be hollow and hemispherical and/or bulbous in structure and made from a flexible and resilient material, such as an elastomeric rubber, e.g., silicone rubber. With additional reference to FIG. 4, which shows pump 124 with face plate 135 of pump body 134 removed, the interior surfaces of filling actuator 130 and portions of interior surfaces of pump body 134 define a first chamber 142 within filling actuator 130 (indicated with dotted lines in FIGS. 1 and 2). For example, pump body 134 may include a first recess 166 that in conjunction with inner surfaces of filling actuator 130 defines first chamber 142. Accordingly, in some embodiments, first chamber 142 is hemispherical and/or bulbous in form. First chamber 142 may have a volume of between approximately 0.1 milliliter and 3 milliliters. In certain embodiments, first chamber 142 may have a volume of approximately 1 milliliter. Similarly, emptying actuator 132 may be hollow and bulbous in structure and made from a flexible and resilient material, such as an elastomeric rubber, e.g., silicone rubber. The interior surfaces of emptying actuator 132 and other portions of interior surfaces of pump body 134 define a second chamber 144 within emptying actuator 132 ((indicated with dotted lines in FIGS. 1 and 2). For example, pump body 134 may include a second recess 168 that in conjunction with inner surfaces of emptying actuator 132 defines second chamber 144. Accordingly, in some embodiments, second chamber 144 is hemispherical and/or bulbous in form. Second chamber 144 may have a volume of between approximately 0.1 milliliter and 3 milliliters. In certain embodiments, second chamber 144 may have a volume of approximately 1 milliliter. In some embodiments, at least first recess 166 and second recess 168 may be fabricated as individual components that are assembled in pump 124. In other embodiments, at least first recess 166 and second recess 168 may be molded integrally into pump 124.

An output port 158 may be disposed through pump body 134 in fluid communication with first chamber 142 of filling actuator 130. An input port 160 may be disposed through pump body 134 in fluid communication with second chamber 144 of emptying actuator 132. Output port 158 and input port 160 may be disposed through a surface of pump body 134 containing first recess 166 and second recess 168. In some embodiments, output port 158 may be centered within first recess 166, and input port 160 may be centered within second recess 168.

Figure 4:
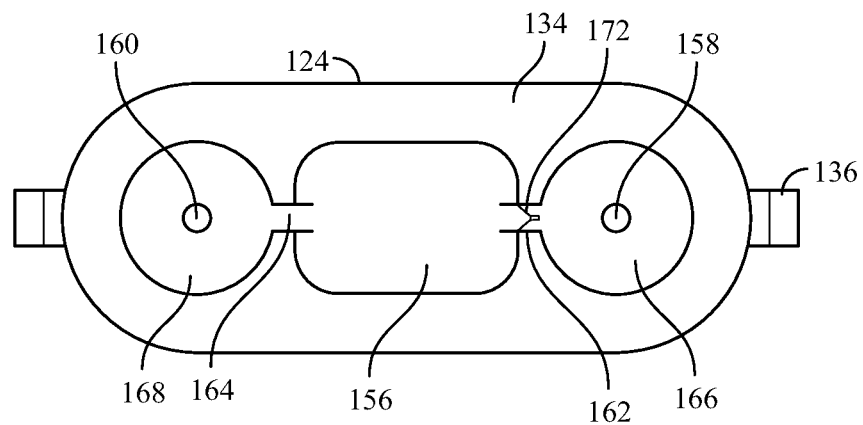
FIG. 4 depicts a front view of a pump without a faceplate that comprises a portion of the hydraulic mechanism of FIG. 2.

Referring to FIG. 2, one end of first tube 126 may be connected to output port 158 of first chamber 142 of filling actuator 130, and the other end of first tube 126 may be connected to tip or first port 138 of barrel 116. One end of second tube 128 may be connected to the second port 140 of barrel 116, and the other end of second tube 128 may be connected to input port 160 of second chamber 144 of emptying actuator 132. As shown in FIG. 4, a bladder 156 may be disposed within pump body 134 between and connected to an inlet 162 of first chamber 142 and an outlet 164 of second chamber 144. This bladder may be flexible, e.g., fabricated from an elastomeric rubber such as silicone rubber. Accordingly, bladder 156 may expand to accommodate fluid that is pumped therein, as explained below.

Mechanism 112 may include a fluid, such as saline, and provide fluid communication between its various components, particularly those mentioned in the preceding paragraph. In some embodiments, the fluid flow is unidirectional. In other embodiments the flow may be bidirectional. Although only unidirectional embodiments are described herein, those of ordinary skill in the art should readily understand that implementation of bidirectional flow embodiments depend primarily upon design choices involving different types of valves (e.g., two way valves and check valves) and actuation mechanisms than those described herein for unidirectional flow.

One unidirectional flow embodiment may include a first backflow valve 171 and a second backflow valve 172. Duckbill valves and check valves are suitable backflow valves. (e.g., B. Braun Part No. S5401033SN). First backflow valve 171 may be positioned in first tube 126, e.g., proximate the output port of first chamber 142, such that the outlet or "bill" of the valve is closer to first port 138 of barrel 116 than the inlet of the valve. Second backflow valve 172 may be positioned within or proximate to inlet 162 of first chamber 142, such that the outlet or "bill" of the valve is closer to first chamber 142 than the inlet of the valve. Accordingly, upon depressing filling actuator 130, fluid contained within first chamber 142 is forced into first tube 126. First valve 171 and second valve 172 ensure that this fluid advances into first tube 126 and not bladder 156. Upon releasing filling actuator 130, fluid may be sucked into first chamber 142 from bladder 156, through inlet 162 and second valve 172. In those embodiments where bladder 156 is not flexible (e.g., a tube) this action may cause back pressure to be generated within bladder 156. Accordingly, second valve 172 should be sufficiently robust to withstand such back pressure. In other embodiments, bladder 156 may be flexible such that bladder 156 may shrink as fluid is removed therefrom, which may assist in removing or eliminating backpressure.

Figure 3:
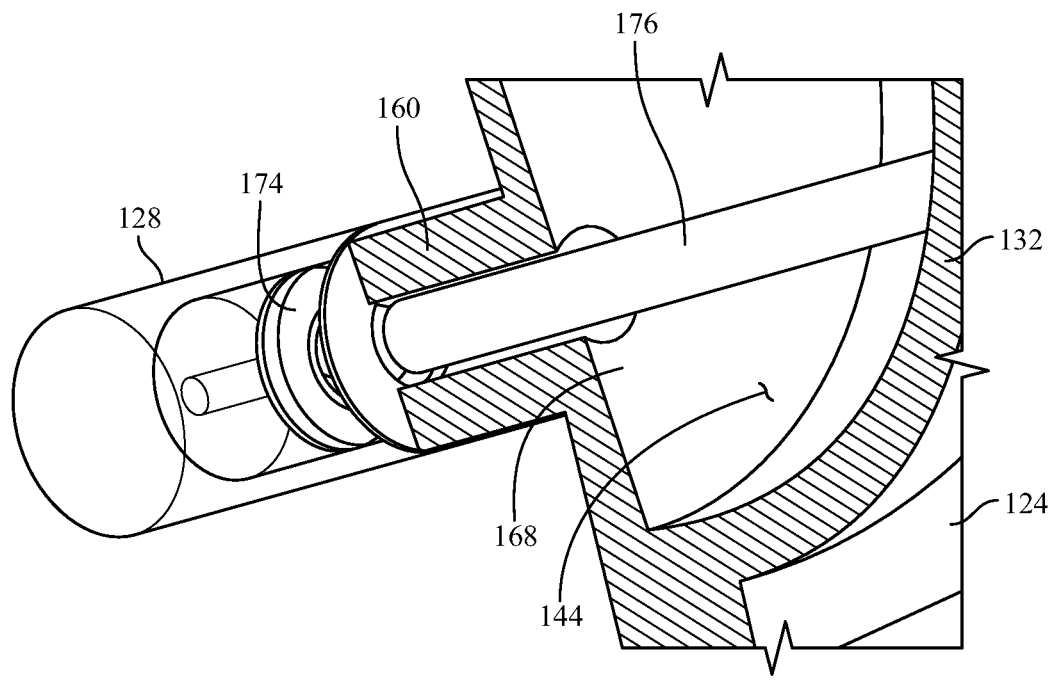
FIG. 3 depicts a magnified perspective cross-sectional view of the hydraulic mechanism of FIG. 2.

FIG. 3 shows an enlarged cross-section view of emptying actuator 132 connected to second tube 128. Another or third valve 174 (also shown in FIG. 2), which in some embodiments may be a backflow valve, but in other embodiments may be a mechanically activated open-close valve (e.g., B. Braun Part No. S5401010SN; Qosina Part Nos. 80063 or 80466), may be disposed within second tube 128. When third valve 174 is in a closed configuration, fluid cannot flow therethrough. Accordingly, in some embodiments including third valve 174, second valve 172 may be excluded. A finger or arm 176 may be included as a feature of emptying actuator 132 that may be displaced to open third valve 174. When third valve 174 is in an open configuration, it does not resist fluid flow. Third valve 174 returns to a closed configuration when emptying actuator 132 is released because arm 176 returns to its original position. Accordingly, when third valve 174 is in an open configuration, fluid may flow from piston cylinder 116, out second port 140, through second tube 128 and into second chamber 144 under pressure provided by piston 114 and biasing member 170. In some embodiments, no valves are disposed between second chamber 144 and bladder 156. Accordingly, and assisted by any back pressure that may have been generated as described in the preceding paragraph, fluid from within second chamber 144 may flow into bladder 156, first chamber 142, and first tube 126 until the forces within mechanism 112—primarily those caused by the spring force upon piston 114—have reached equilibrium. In some embodiments, equilibrium exists when piston 114 is disposed against tip 138. In some embodiments, equilibrium exists when bladder 156 expands to a maximum volume equal to approximately the volume of barrel 116 as fluid is forced therein under pressure from the spring force upon piston 114.

In some embodiments, mechanism 112 is oriented within implant 100 such that filling actuator 130 and emptying actuator 132 are disposed proximate membrane 104 of shell 102. In some embodiments, filling actuator 130 and emptying actuator 132 may contact an inner surface of membrane 104. Accordingly, a user in whom implant 100 is implanted may actuate actuators 130 and 132 by pressing her skin proximate the desired actuator.

In some embodiments, a standard medical syringe may be used to supply various components of mechanism 112, including, but not limited to, piston 114, barrel 116, and plunger rod 120. In these embodiments, barrel cap 118 should be fastened to barrel 116 such that barrel cap 118 and barrel 116 remain stationary relative to each other. For example, barrel cap 118 may be bonded via, e.g., glue or ultrasonic welding, to barrel 116. Alternatively, barrel 116 and barrel cap 118 may be provided with screw threading such that barrel cap 118 may be screwed onto barrel 116.

Band 108 may include a first end 146 and a second end 148. First end 146 may be connected to a stationary component or feature of mechanism 112, such as barrel cap 118. In some embodiments, barrel cap 118 includes an extension arm or bracket 119 to which first end 146 may be attached. Second end 148 may be connected to a moveable feature or component of mechanism 112, such as plunger cap 122. In some embodiments, plunger cap 122 includes an extension arm or bracket 123 to which second end 148 may be attached. Because piston 114, plunger rod 120, and plunger cap 122 may move relative to barrel 116 and barrel cap 118, first end 146 may move relative to second end 148. Accordingly, this movement may be used to increase or decrease diameter θ of band 108. That is, when distance between plunger cap 122 and barrel cap 118 increases, diameter θ decreases, which causes a corresponding increase in height of shell 102. Conversely, when distance between plunger cap 122 and barrel cap 118 decreases, diameter θ increases, which causes a corresponding decrease in height of shell 102.

Figure 5A:
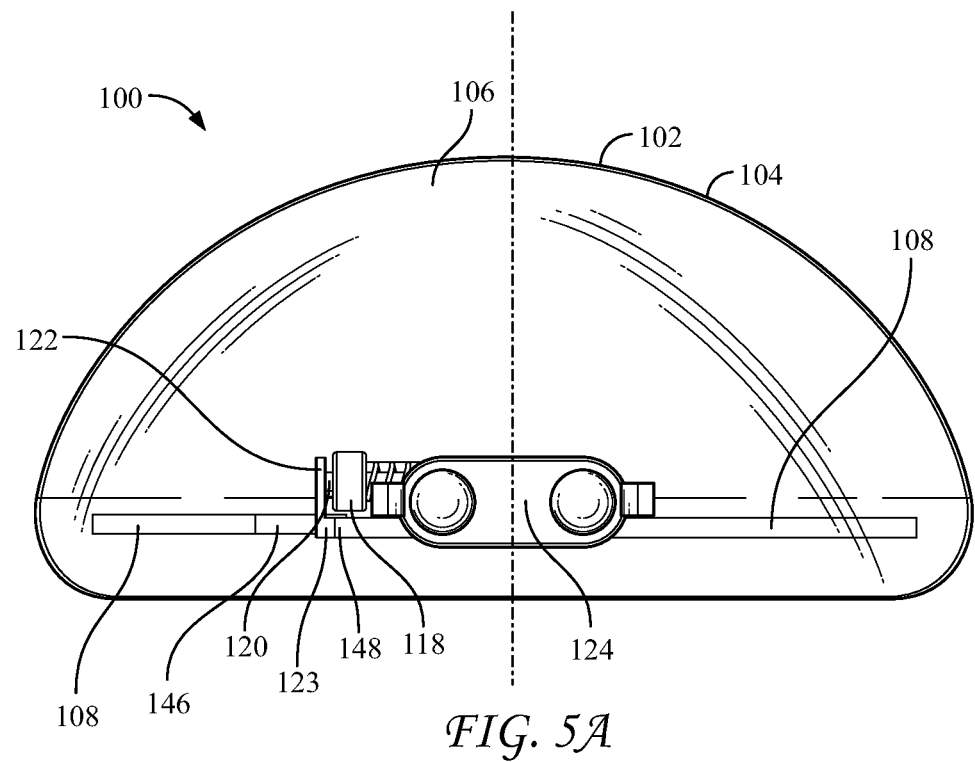
FIG. 5A depicts a front view of the adjustable implant of FIG. 1 having the original profile.
Figure 5B:
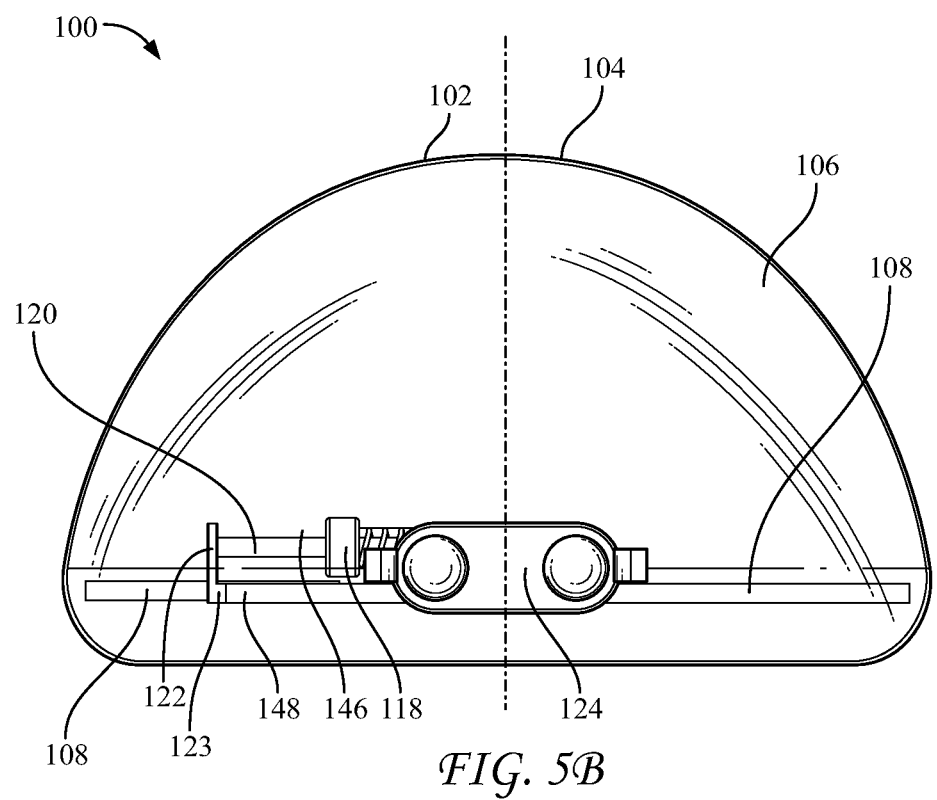
FIG. 5B depicts a front view of the adjustable implant of FIG. 1 having a heightened profile.

FIGS. 5A and 5B reflect two different profiles of adjustable implant 100. The profile of implant 100 may be changed from an original profile, reflected in FIG. 5A, to a heightened profile reflected in FIG. 5B. This change in profile is effected by reducing diameter θ of band 108 using mechanism 112. The original profile may be recovered by enlarging the diameter θ of band 108 using mechanism 112. Intermediate profiles (not shown) may also be achieved by reducing diameter θ less than is required to achieve the heightened profile. Accordingly, a subject may change the profile of implant 100 to her desired preference by using mechanism 112 to change diameter θ of band 108.

Implant 100 may be used according to the following exemplary method. First, implant 100 may be provided. Second, filling actuator 130 may be depressed, which expels fluid contained within first chamber 142 into first tube 126. In typical usage, a volume of fluid roughly equal to or slightly less than the volume of first chamber 142 may be expelled. In turn, fluid within first tube 126 may be advanced through tip 138 and into barrel 116, filling barrel 116, causing displacement of piston 114 toward barrel cap 118 and displacement of plunger cap 122 away from barrel cap 118. Displacement of plunger cap 122 causes a corresponding displacement of second end 148 of band 108. This displacement of second end 148 occurs relative to barrel cap 118 whereas first end 146 is maintained stationary relative to barrel cap 118 because first end 146 is connected to barrel cap 118. Thus, second end 148 moves relative to first end 146, which causes diameter θ of band 108 to decrease and a corresponding increase in the height of shell 102.

Third, filling actuator 130 may be released, which draws fluid from bladder 156 into first chamber 142. In typical usage, a volume of fluid roughly equal to or slightly less than the volume of first chamber 142 may be drawn from bladder 156. First valve 171 prevents fluid from first tube 126 from flowing back into first chamber 142. Fourth, filling actuator 130 may be repeatedly depressed and released, or palpitated, multiple times, e.g., between one more time and approximately and 30 more times. Repeated full or partial palpitations of filling actuator 130 causes barrel 116 to become filled with fluid. With each depression, piston 114 and plunger cap 122 are further displaced. In some embodiments, approximately half of a palpitation, one palpitation, five palpitations, or ten palpitations results in a maximum fluid transfer into barrel 116 and maximum displacement of piston 114. In some embodiments, the maximum displacement of piston 114 occurs when piston 114 abuts barrel cap 118.

Fifth, emptying actuator 132 may be depressed. This step may occur when any volume of fluid is contained within barrel 116, e.g., when barrel 116 is partially filled with fluid, when barrel 116 is completely filled with fluid, when piston 114 does not abut barrel cap 118, or when piston 114 abuts barrel cap 118. Depressing emptying actuator 132 displaces finger or arm 176 to open third valve 174 and allow fluid communication between barrel 116, second port 140, second tube 128, and second chamber 144 of emptying actuator 132. Thus, biasing member 170 pushes piston 114 toward tip 138, expelling fluid from barrel 116 out of second port 140 and into second tube 128. Fluid already in second tube 128 may be advanced into second chamber 144 of emptying actuator 144 and into bladder 156. Emptying actuator 132 may be palpitated quickly or held down for longer periods of time. So long as emptying actuator 132 is depressed and third valve 174 is open while fluid is within barrel 116, piston 114 under the force of biasing member 170, expels fluid from barrel 116 out through second port 140. In those embodiments where bladder 156 is flexible, this may cause bladder 156 to expand because the spring force upon piston 114 may cause pressure within bladder 156 sufficient to cause bladder 156 to expand. Further, as piston 114 is displaced toward tip 138, plunger cap follows, causing relative movement between second end 148 and first end 146 of band 108. This increases the diameter θ of band 108, which causes a corresponding decrease in the height of shell 102.

The foregoing method may be applied by a subject in whom implant 100 is implanted to change the height of the implant. Correspondingly, she may change the projection of her breast. For example, the subject may begin with implant 100 having a configuration in which band 108 has a maximum diameter θ such that the height of shell 102 is a minimum. To increase the projection of her breast, the subject may depress filling actuator 130 at least one time to decrease the diameter θ of band 108 and increase the height of shell 102. For example, if the subject would like her breast to project further from her body, the subject may partially palpitate filling actuator 130, which, in some embodiments, may cause the height of shell 102 to increase about a quarter to one third from its minimum height toward its maximum height. Alternatively, if the subject would like her breast to project from her body even further, the subject may palpitate filling actuator 130 between approximately one to two times, which, in some embodiments, may cause the height of shell 102 to increase to its maximum height.

After the subject has increased the profile of her breast, she may decide that she would like to reduce the profile her breast. To do so, she may depress emptying actuator 132 until her breast has reached the profile she desires. However, if she shrinks the profile of her breast much, she may enlarge it to the desired size by again actuating actuator 130. In this manner, she may "fine tune" the profile of her breast. Further, she may do so whenever she desires to change the profile of her breast because the adjustability of implant 100 is a permanent feature of the implant that cannot be removed. This is so because adjustable implant 100 is entirely self-contained, like a conventional permanent implant, but unlike conventional tissue expanders or the Becker Expander/Mammary Prostheses. No fluids, liquids, or other materials are introduced or removed from within the boundary defined by shell membrane 104 in order to change the profile of implant 100.

Figure 6:
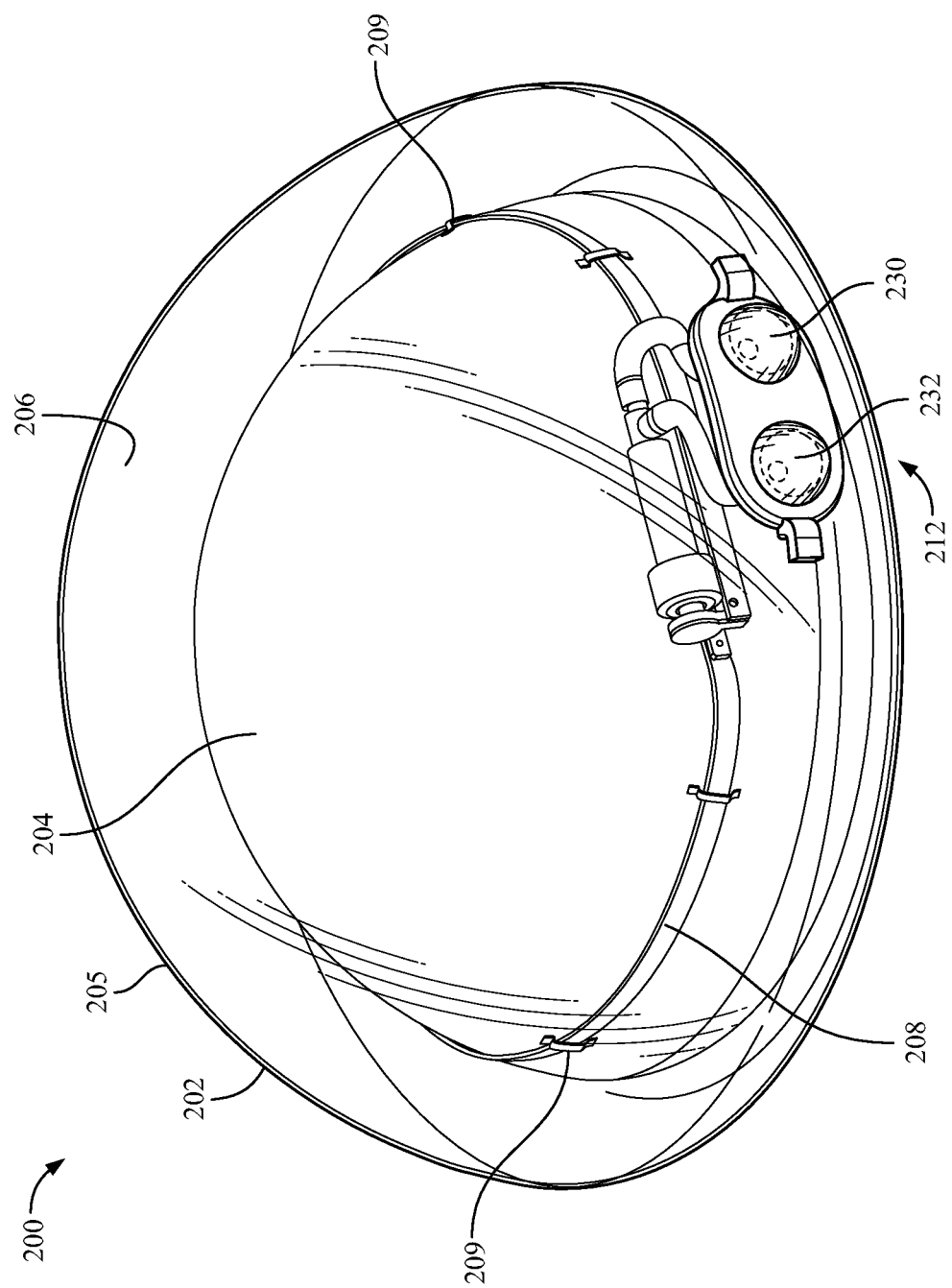
FIG. 6 depicts a perspective view of an alternate embodiment of an adjustable implant.

FIG. 6 shows an alternate embodiment of an adjustable implant. Implant 200 includes a shell 202 having two membranes, an inner or first membrane 204 and an outer or second membrane 205 that surrounds inner membrane 204. Both inner membrane 204 and out membrane 205 are filled with material 206. Band 208 is disposed about and proximate to inner membrane 204. In some embodiments, loops 209 may be circumferentially distributed about and attached to inner membrane 204 such that band 208 is further disposed within loops 209. A hydraulic mechanism 212 may be used to change a diameter of band 208 to change the profile of inner membrane 204, which in turn changes the profile of outer membrane 205 and the overall profile of implant 200. In some embodiments, mechanism 212 is disposed between inner membrane 204 and outer membrane 205 such that filling actuator 230 and emptying actuator 232 are proximate an inner surface of outer membrane 205.

Figure 7:
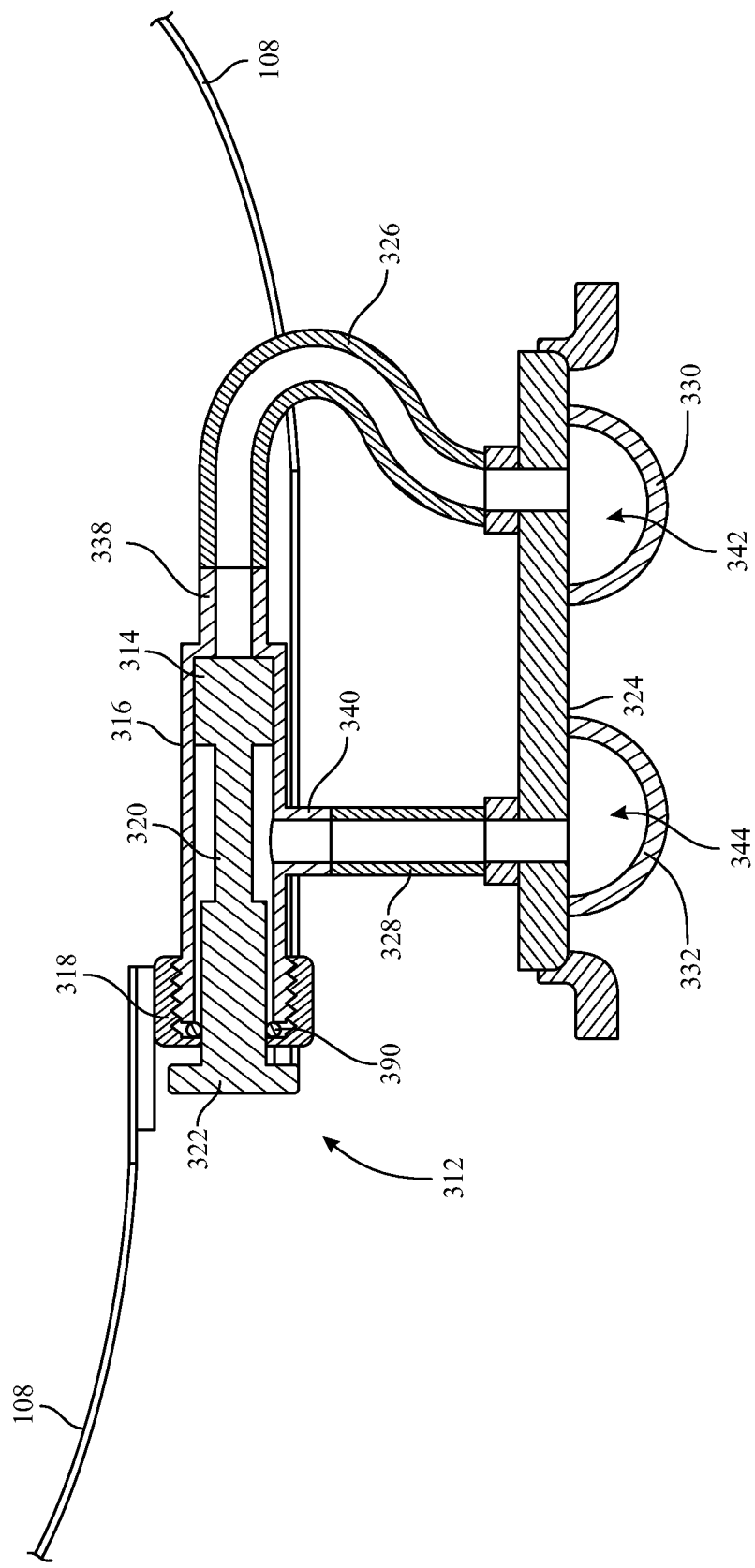
FIG. 7 depicts a magnified cross-section view of an alternate embodiment of hydraulic mechanism within an adjustable implant.

FIG. 7 shows a cross-section of an alternate embodiment of a hydraulic mechanism that may be used to change the diameter of band 108. The connections between mechanism 312 and band 108 are similar to the connections between mechanism 112 and band 108. Accordingly, these connections are not detailed in FIG. 7. Mechanism 312 includes a pump 324 that has a first actuator 330 that defines a first chamber 342 and a second actuator 332 that defines a second chamber 344. Mechanism 312 also includes a first tube 326 that connects first chamber 342 to first port 338 of barrel 316, and a second tube 328 that connects a second port 340 of barrel 316 to second chamber 344.

Differences in structure between mechanism 312 and 112 include: 1) the distance between second port 340 and first port 338 compared to the distance between second port 140 and first port 138 of mechanism 112 (FIG. 2); 2) first chamber 342 and second chamber 344 are not connected within pump 324, whereas first chamber 142 and second chamber 144 are connected within pump 124; and 3) mechanism 312 lacks a biasing member or spring akin to biasing mechanism or spring 170. Further, in some embodiments, mechanism 312 does not have a bladder akin to bladder 156.

In some embodiments, mechanism 312 includes a sealing device or devices. For example, a first seal may be an o-ring 390 that may be provided between plunger rod 320 and barrel cap 318. O-ring 390 has two purposes. First, it helps prevent fluid from leaking out of mechanism 312 from between plunger rod 320 and barrel 316 and into implant material 106. Second, it helps prevent any portion of material 106, which may be a silicone gel, from being sucked into barrel 316. In some embodiments, a cylindrical bellows component may be disposed about plunger rod 320 and connected on one end to barrel cap 318 and on the other end to plunger cap 322. Thus, as plunger cap 322 is displaced away from barrel cap 318, the bellows component elongates. As plunger cap 322 is displaced toward barrel cap 318, the bellows component shortens. The bellows component may further help prevent any portion of material 106 from being sucked into barrel 316, and it may reduce the force necessary to displace plunger rod 320 and plunger cap 322 through material 106. A second seal (not shown) may be disposed circumferentially about piston 314. This seal may be an integral part of piston 314, typical of standard medical syringes, which include pistons made of rubber, e.g., silicone rubber. This prevents any fluid from flowing between piston 314 and barrel 316, such that hydraulic pressure may be generated on both sides of plunger 314 by depressing first actuator 330 or second actuator 332. Such sealing mechanisms may also be incorporated into other embodiments, including those of mechanism 112.

Fluid may be disposed within chambers 342 and 344 and tubes 326 and 328. Fluid may also be disposed within barrel 316 between piston 314 and barrel cap 318. Depression of first actuator 330 drives fluid contained therein into first tube 326, which causes fluid within first tube 326 to pass through first port 338, displace piston 314 toward barrel cap 318, and advance and into barrel 316. Depression of second actuator 332 drives fluid contained therein into second tube 328, which causes fluid within second tube 328 to pass through second port 340 and into barrel 316 between barrel cap 318 and piston 314, which displaces piston 314 toward first port 338. Accordingly, first actuator 330 may be used to drive piston 314 in a first direction (i.e., to the left in FIG. 7) and second actuator 332 may be used to drive piston 314 in a reverse or second direction (i.e., to the right in FIG. 7). As piston 314 is driven in the first direction, fluid contained between piston 314 and barrel cap 318 may be driven out of barrel 316 via second port 340. As piston 314 is driven in the second direction, fluid may be driven out of barrel 316 via first port 338. Seals and/or valves may be incorporated into mechanism 312 to help prevent or minimize fluid from being withdrawn prematurely from barrel 316 as either the first actuator 330 or second actuator 332 is released following a depression.

Chambers 142, 144, 342, and 344, may have volumes equivalent to each other or different from each other. For example, these chambers may have volumes of between 0.5 ml and 10 ml. In certain embodiments, these chambers may have volumes of approximately 1 ml. The inventors have fabricated a prototype in which the volumes of these chambers are approximately 1.1 ml.

A proof of concept experiment was conducted upon the prototype, which helped determine a correlation between: 1) the volume of fluid in the chambers (e.g., 142 and 342); 2) a distance a piston (e.g., 114 and 314) of a 1 ml syringe may be moved, which corresponds to a change in circumference of a band (e.g., 108) wrapped around a 400 cc implant (e.g., 100); and 3) an increase in height of the implant. It was determined that the piston of the 1 ml syringe traversed a distance of approximately 58 mm as it was filled from 0 ml to 1 ml. It was also determined that reducing the band's circumference by approximately 53 mm caused a height increase in the implant of approximately 10 mm. This suggests that approximately 0.92 ml of fluid may be disposed within the chambers, which may be used to increase the height of a 400 cc implant by 10 mm.

Further experiments were conducted upon various implants to determine correlations between decreases to the band's diameter and increases to the implant's height. In each instance, a band was wrapped around the widest portion of various implants. The first implant was a 350 cc implant having a diameter of approximately 117 mm and a height of approximately 45 mm. By reducing the diameter of this implant to approximately 105 mm, the height was increased to approximately 59 mm. The second implant was a 400 cc implant having a diameter of approximately 123 mm and a height of approximately 46 mm. By reducing the diameter of this implant to approximately 108 mm, the height was increased to approximately 60 mm. The third implant was a 465 cc implant having a diameter of approximately 124 mm and a height of approximately 55 mm. By reducing the diameter of this implant to approximately 111 mm, the height was increased to approximately 65 mm.

It should be understood that any of the examples and/or embodiments described herein may include various other features in addition to or in lieu of those described above. The teachings, expressions, embodiments, examples, etc. described herein should not be viewed in isolation relative to each other. Various suitable ways in which the teachings herein may be combined should be readily apparent to those of ordinary skill in the art in view of the teachings herein.

Having shown and described exemplary embodiments of the subject matter contained herein, further adaptations of the methods and systems described herein may be accomplished by appropriate modifications without departing from the scope of the claims. Some such modifications should be apparent to those skilled in the art. For instance, the examples, embodiments, geometrics, materials, dimensions, ratios, steps, and the like discussed above are illustrative. Accordingly, the claims should not be limited to the specific details of structure and operation set forth in the written description and drawings.

We claim:

1. An adjustable implant, comprising:
    a shell including a base and having a first diameter in a plane parallel to the base, the shell further including a first membrane,
    a hydraulic mechanism disposed within the shell, the mechanism including a first component and a second component that is moveable with respect to the first component; and
    a band disposed within the shell in a round configuration having a second diameter in the plane that is less than the first diameter, the band having a first end and a second end,
    wherein the first end of the band is connected to the first component and the second end of the band is connected to the second component,
    wherein the mechanism includes a fluid and a pump having a first actuator comprising a first chamber and a second actuator comprising a second chamber, and
    wherein the first component comprises a barrel and the second component comprises a piston disposed at least partially within the barrel, and wherein the piston further includes a plunger rod and a plunger cap and the barrel further includes a barrel cap, a first port, and a second port.

2. The adjustable implant of claim 1, wherein the mechanism further includes a first tube connected between the first chamber and the first port and a second tube connected between the second port and the second chamber.

3. The adjustable implant of claim 2, further comprising a loop through which the band is disposed.

4. The adjustable implant of claim 3 wherein the loop is attached to the first membrane.

5. The adjustable implant of claim 4, wherein the shell further comprises a second membrane surrounding the first membrane.

6. The adjustable implant of claim 5, wherein the mechanism further includes a biasing member in the barrel between the piston and the barrel cap, and a bladder connecting the first chamber to the second chamber.

7. The adjustable implant of claim 6, wherein the second actuator includes a finger for opening a valve disposed in the second tube.

8. The adjustable implant of claim 7, wherein the round configuration is an elliptical configuration.

9. An adjustable implant, comprising:
    a shell including a first membrane filled with an elastomer;
    a hydraulic mechanism disposed within the shell, the mechanism including a pump, a piston, and a barrel; and
    an adjustable band disposed within the shell in a round configuration having a first end connected to the barrel and a second end connected to the piston.

10. The adjustable implant of claim 9, further comprising a loop through which the band is disposed.

11. The adjustable implant of claim 10 wherein the loop is attached to the first membrane.

12. The adjustable implant of claim 11, wherein the shell further comprises a second membrane surrounding the first membrane.

13. A method of using an adjustable implant, comprising:
    providing an implant having a height and including therein an adjustable band having a round configuration and a diameter;
    decreasing the diameter of the band; and
    increasing the height of the implant,
    wherein the implant includes:
        a shell including a base and having a first diameter in a plane parallel to the base, the shell further including a first membrane;
        a hydraulic mechanism disposed within the shell, the mechanism including
            a barrel having a barrel cap, a first port, and a second port, and a piston at least partially disposed within the barrel including a plunger rod and plunger cap,
            a fluid,
            a pump having a first actuator including a first chamber and a second actuator including a second chamber; and
    wherein the band includes a first end connected to the barrel cap and a second end connected to the plunger cap.

14. The method of claim 13, further comprising
    depressing the first actuator; and
    depressing the second actuator.

15. The method of claim 14, wherein depressing the first actuator advances fluid into the barrel and causes the piston, plunger cap, and the second end of the band to move in a first direction.

16. The method of claim 15, wherein depressing the second actuator causes the piston, plunger cap, and the second end of the band to move in a direction opposite the first direction.

* * * * *